United States Patent [19]

Sato et al.

[11] Patent Number: 5,273,897
[45] Date of Patent: Dec. 28, 1993

[54] PRODUCTION OF AN ESTERASE IN A CULTURE MEDIUM CONTAINING AN ESTER OF SORBITAN OR POLYOXYETHYLENE SORBITAN AND A FATTY ACID ALONG WITH AN AMINO ACID

[75] Inventors: Motoyoshi Sato, Tokyo; Kouhei Takahashi, Kawagoe; Takeji Shibatani, Kobe; Kouji Yanagiya, Ageo, all of Japan

[73] Assignee: Tanabe Seiyaku Co., Ltd., Osaka, Japan

[21] Appl. No.: 739,459

[22] Filed: Aug. 2, 1991

[30] Foreign Application Priority Data

Aug. 10, 1990 [JP] Japan .................... 2-213266

[51] Int. Cl.$^5$ .................... C12N 9/16; C12N 1/00; C12N 1/20
[52] U.S. Cl. .................... 435/196; 435/243; 435/252.32; 435/254.8; 435/253.3
[58] Field of Search ............... 435/196, 243, 822, 880, 435/881, 843, 874, 252.32, 252.34

[56] References Cited

U.S. PATENT DOCUMENTS

| | | | |
|---|---|---|---|
| 4,803,275 | 2/1989 | Kanamaru et al. | 546/116 |
| 5,013,757 | 5/1991 | Kanamaru et al. | 514/568 |
| 5,110,722 | 5/1992 | Brockbank et al. | 435/1 |

FOREIGN PATENT DOCUMENTS

| | | |
|---|---|---|
| 52974 | 11/1981 | European Pat. Off. |
| 245793 | 5/1987 | European Pat. Off. |
| 62-118884 | 5/1987 | Japan |
| 1-181788 | 1/1988 | Japan |
| 1571877 | 4/1978 | United Kingdom |

OTHER PUBLICATIONS

Archiv. Biochem. Biophys., vol. 160, pp. 504-513 (1974).
J. Biochem., vol. 95, pp. 1047-1054 (1984).

*Primary Examiner*—David M. Naff
*Assistant Examiner*—Michael V. Meller
*Attorney, Agent, or Firm*—Birch, Stewart, Kolasch & Birch

[57] ABSTRACT

A process for producing an esterase by cultivating an esterase-producing microorganism is disclosed. The cultivation is carried out in a medium to which has been added an ester of sorbitan or polyoxyethylene sorbitan and a substituted or unsubstituted fatty acid having 12 to 18 carbon atoms along with an amino acid which has the formula:

$$\begin{array}{c} R^1-CH-COOH \\ | \\ R^2-NH \end{array} \qquad [I]$$

wherein $R^1$ is hydrogen or a lower alkyl group which may be substituted with a substituent selected from the group consisting of hydroxy, carboxy, amino, guanidino, carbamoyl, mercapto, methylthio, phenyl, hydroxyphenyl, imidazolyl and indolyl, and $R^2$ is hydrogen, or $R^1$ and $R^2$ are combined to form trimethylene.

8 Claims, No Drawings

PRODUCTION OF AN ESTERASE IN A CULTURE MEDIUM CONTAINING AN ESTER OF SORBITAN OR POLYOXYETHYLENE SORBITAN AND A FATTY ACID ALONG WITH AN AMINO ACID

This invention relates to an improved process for producing esterase.

Esterase catalyzes the hydrolysis of ester, esterification reaction of an organic acid and an alcohol, and ester exchange. Recently, attempts have been made to use esterase as a catalyst for organic synthetic reaction. For example, esterase has been used to prepare optically active methyl (2R,3S)-3-(4-methoxyphenyl)glycidate from racemic methyl 3-(4-methoxyphenyl)glycidate (European Patent Publication No. 362,556 A2).

Such esterases include, for example, those obtained from the microorganisms belonging to genera such as Arthrobacter, Bacillus, Pseudomonas, Serratia, Corynebacterium, Micrococcus, Absidia, Mucor, Candida, Rhizopus, and the like [Japanese Patent Publication (unexamined) No. 181788/1989, Archiv. Biochem. Biophys. 160, 504–513(1974), J. Biochem. 95, 1047–1054(1984)]. However, in comparison with other enzymes such as protease or cellulase, esterase is generally more expensive and disadvantageous to use for industrial purposes, because the known microorganisms have in general low esterase-productivity.

As a result of various investigations, the present inventors have found that esterase can be produced in higher yield by cultivating an esterase-producing microorganism in a medium to which an amino acid is added, and also that the esterase-productivity of said microorganism can be further improved by adding a fatty acid or an ester thereof to the medium together with an amino acid.

According to the present invention, esterase can be produced in high yield by cultivating an esterase-producing microorganism in a medium to which (1) an amino acid or (2) an amino acid and a fatty acid or an ester thereof is/are added.

As the amino acid to be used in the present invention, there can be employed a naturally occurring protein α-amino acid including an amino acid of the formula:

$$R^1-CH-COOH \qquad [I]$$
$$\quad\;|$$
$$R^2-NH$$

wherein $R^1$ is hydrogen or a lower alkyl group which may be substituted with a substituent selected from the group consisting of hydroxy, carboxy, amino, guanidino, carbamoyl, mercapto, methylthio, phenyl, hydroxyphenyl, imidazolyl and indolyl, and $R^2$ is hydrogen, or $R^1$ and $R^2$ are combined to form trimethylene. Examples of such amino acid include glycine, alanine, valine, leucine, isoleucine, serine, threonine, cysteine, arginine, asparagine, glutamine, aspartic acid, glutamic acid, phenylalanine, tyrosine, histidine, tryptophan, proline, lysine, methionine and the like. Preferred examples of such amino acid include, for example, glycine, alanine, threonine, proline, histidine, arginine, serine, glutamic acid, aspartic acid and the like. These amino acids can be used either alone or as a mixture of more than two amino acids.

These amino acids can be used either in the free form or in the form of a salt thereof. Examples of the salt thereof include an acid addition salt (e.g., hydrochloride, sulfate, and the like), an alkali metal salt (e.g., sodium salt, potassium salt), an alkaline earth metal salt (e.g., calcium salt, magnesium salt), and the like.

Moreover, these amino acids may be L-amino acids, but the amino acids to be used in the present invention are not limited to L-amino acids. A mixture of L-amino acids and D-amino acids including racemic amino acids can also be used in the present invention, because D-isomers are considered to have no substantial effect on esterase-productivity of microorganisms.

As the fatty acid to be used for the purpose of the present invention, there can be employed a saturated or unsaturated fatty acid having 12 to 18 carbon atoms, including $C_{12-18}$ alkanoic acid, $C_{12-18}$ alkenoic acid, $C_{12-18}$ alkadienoic acid and $C_{12-18}$ alkatrienoic acid. Examples of the fatty acid include lauric acid, myristic acid, palmitic acid, stearic acid, oleic acid, linoleic acid, linolenic acid, ricinolic acid and the like. Preferred examples of fatty acid include stearic acid, oleic acid, linoleic acid, linolenic acid and the like.

As the fatty acid ester to be used for the purpose of the present invention, there can be employed an ester of sorbitan or polyoxyethylene sorbitan and a saturated or unsaturated fatty acid having 12 to 18 carbon atoms, including an ester of sorbitan or polyoxyethylene sorbitan and fatty acid such as $C_{12-18}$ alkanoic acid, $C_{12-18}$ alkenoic acid, $C_{12-18}$ alkadienoic acid and $C_{12-18}$ alkatrienoic acid. Examples of the fatty acid ester include an ester of sorbitan or polyoxyethylene sorbitan and fatty acid such as lauric acid, myristic acid, palmitic acid, stearic acid, oleic acid, linoleic acid, linolenic acid, ricinolic acid, stearic acid, oleic acid, linoleic acid, linolenic acid and the like. Preferred examples of the fatty acid ester include sorbitan monolaurate, sorbitan monomyristate, sorbitan monostearate, sorbitan tristearate, sorbitan monooleate, sorbitan trioleate, polyoxyethylene sorbitan monolaurate, polyoxyethylene sorbitan monomyristate, polyoxyethylene sorbitan monostearate, polyoxyethylene sorbitan monooleate, polyoxyethylene sorbitan trioleate and the like.

The amount of a fatty acid or an ester thereof to be used in the present invention is about 0.1 g to 10 g, preferably about 0.5 g to 2 g, per liter of the medium, respectively.

Any microorganisms which have ability to produce esterase can be used in the present invention. For example, microorganisms such as molds, bacteria, yeasts and actinomycetes having such ability can be suitably employed. Specifically, these microorganisms include molds belonging to the genera Absidia, Aspergillus, Fusarium, Gibberella, Mucor, Neurospora, Trichoderma, Rhizopus, bacteria belonging to the genera Achromobacter, Alcaligenes, Bacillus, Brevibacterium, Corynebacterium, Providencia, Pseudomonas, Serratia, yeast belonging to the genera Candida, Saccharomycopsis, and actinomycetes belonging to the genus Nocardia. Specific examples of such microorganism include, for example, Absidia corymbifera IFO 4009, Absidia corymbifera IFO 4010, Aspergillus ochraceus IFO 4346, Aspergillus terreus IFO 6123, Fusarium oxysporum IFO 5942, Fusarium oxysporum ATCC 659, Fusarium solani IFO 5232, Gibberella fujikuroi IFO 5268, Mucor angulimacrosporus IAM 6149, Mucor circinelloides IFO 6746, Mucor flavus IAM 6143, Mucor fragilis IFO 6449, Mucor genevensis IAM 6091, Mucor globosus IFO 6745, Mucor hiemalis OUT 1045, Mucor hiemalis OUT 1047, Mucor janssenii OUT 1050, Mucor janssenii IFO 5398, Mucor javanicus IFO 4569, Mucor javanicus IFO 4570, Mucor javanicus IFO 4572, Mucor javanicus IFO 5382, Mucor lamprosporus IEO 6337, Mucor petrinsularis IFO 6751, Mucor plumbeus IAM 6117, Mucor praini IAM 6120, Mucor pusillus IAM 6122, Mucor racemosus IFO 4581, Mucor ramannianus IAM 6128, Mucor recurvus IAM 6129, Mucor silvaticus IFO 6753, Mucor spinescens IAM 6071, Mucor subtilissimus IFO 6338, Neurospora crassa IFO 6068, Rhizopus arrhizus IFO 5780, Rhizopus delemar ATCC 34612, Rhizopus japonicus IFO 4758, Trichoderma viride OUT 4208, Trichoderma viride IFO 4847, Achromobacter cycloclastes IAM 1013, Alcaligenes faecalis OUT 8030, Bacillus sphaericus IFO 3525, Bacillus subtilis OUT 8104, Bacillus subtilis OUT 8106, Brevibacterium ketoglutamicum ATCC 15588, Corynebacterium alkanolyticum ATCC 21511, Corynebacterium hydrocarboclastum ATCC 15992, Corynebacterium primorioxydans ATCC 31015, Providencia alcalifaciens JCM 1673, Pseudomonas mutabilis ATCC 31014, Pseudomonas putida ATCC 17426, Pseudomonas putida ATCC 17453, Pseudomonas putida ATCC 33015, Serratia liquefaciens ATCC 27592, Serratia marcescens ATCC 13880, Serratia marcescens ATCC 14764, Serratia marcescens ATCC 19180, Serratia marcescens ATCC 21074, Serratia marcescens ATCC 27117, Serratia marcescens ATCC 21212, Serratia marcescens FERM BP-487, Serratia prymutica IAM 1255, Candida parapsilosis IFO 0585, Candida boidinii IFO 10240, Saccharomycopsis lipolytica IFO 0717, Saccharomycopsis lipolytica IFO 0746, Saccharomycopsis lipolytica IFO 1195, Saccharomycopsis lipolytica IFO 1209, Saccharomycopsis lipolytica IFO 1548, Nocardia asteroides IFO 3384, Nocardia asteroides IFO 3424, Nocardia asteroides IFO 3423 and Nocardia gardneri ATCC 9604.

Among them, preferred examples of the microorganism to be used in the present invention are those belonging to genus Absidia, Mucor, Corynebacterium, Pseudomonas and Serratia.

These microorganisms may be either wild strains, mutant thereof or those derived from the microorganisms according to the bioengineering methods such as recombination and cell fusion.

Any medium, i.e., a medium containing the sources of carbon and nitrogen, in which the esterase-producing microorganisms of the present invention can grow and proliferate may be used as the medium for the cultivation. Suitable examples of the carbon source include sugars such as dextrin, glucose, sucrose, organic acids such as fumaric acid, citric acid or succinic acid, and the like. Inorganic salts such as ammonium sulfate, ammonium chloride or ammonium nitrate, peptone, corn steep liquor, yeast extract, casein hydrolysate and the like can be used as the nitrogen source. It is preferred to use 0.5 to 15 w/v %, more preferably 1.0 to 10 w/v % of the carbon source, and 0.1 to 5.0 w/v %, more preferably 0.1 to 2.0 w/v % of nitrogen source. If required, inorganic salts such as phosphates, magnesium salts, potassium salts, calcium salts and the like, or metal ions such as iron ions, manganese ions, copper ions, nickel ions, zinc ions and the like may be added to the medium.

Cultivation of the microorganism in the medium to which (1) an amino acid, or (2) an amino acid and a fatty acid or an ester thereof is/are added can be carried out in a conventional manner. The conditions of cultivation may vary depending on a kind of the medium, microorganism and the like. But it is usually preferred to carry it out at pH of about 5 to 8, under aerobic condition, and at room temperature or under moderate heating, more preferably at a temperature of about 20° C. to 40° C.

It is appropriate to recover esterase at the post-log phase or stationary phase of the microbial growth, when the esterase accumulation inside or outside the microbial cells become maximum.

The esterase accumulated inside or outside the microbial cells can be recovered by per se known method as either a crude enzyme solution, microbial cells or the processed product of microbial cells. For example, the esterase accumulated outside of the microbial cells can be recovered by removing cells from the broth by centrifugation, microfiltration with microfilter (e.g., EMP-113 manufactured by Asahi Chemical Industry Ltd., NTM9002C-1 manufactured by Nitto Denko Corporation), and the like, and if required, condensing the supernatant solution by ultrafiltration with an ultrafilter (e.g., SIP-1013 manufactured by Asahi Chemical Industry Ltd., NTU 2020 manufactured by Nitto Denko Corporation).

Further, if required, the esterase may be isolated or purified from the crude enzyme solution by means of salting-out with inorganic salt (e.g., ammonium sulfate, an alkali metal sulfate or an alkali metal halide), differential precipitation with a hydrophilic organic solvent (e.g., an alcohol or acetone), column chromatography with an ion exchange resin or hydrophobic resin, gel filtration, protein precipitation with nucleic acid or tannin, or a combination of these methods. The enzymes thus obtained may be, if required, further purified by isoelectric precipitation, dialysis, electrodialysis, electrophoresis and the like.

As compared with the processes wherein no amino acid is added to the medium, the process of the present invention is advantageous in that esterase can be produced in a remarkably higher yield because of the improved esterase-productivity of the microorganisms. For example, by the process of the present invention wherein L-prorine (1 w/v %) and polyoxyethylene sorbitan monooleate (0.5 v/v %) are added to the medium, esterase was produced in about 3.6 times higher yield than by the process wherein no amino acid is added to the medium.

Esterase produced by the process of the present invention can be used for a variety of industrial purposes, for example, as a medicine, as a catalyst for hydrolysis, esterification and so forth. For example, it can be used to prepare optically active 3-phenylglycidic acid esters such as methyl (2R, 3S)-3-(4-lower alkoxy-phenyl)-glycidate which is an important intermediate in the synthesis of a cardiovascular agent known as diltiazem hydrochloride [chemical name: (+)-cis-2-(4-methoxyphenyl)-3-acetoxy-5-[2-(dimethylamino)ethyl]-2,3-dihydro-1,5-benzothiazepine-4(5H)-one hydrochloride].

Throughout the present specification and Claims, the term 'lower alkyl group' should be interpreted as referring to alkyl group having 1 to 4 carbon atoms.

The following Examples further illustrate the present invention in details but are not to be construed to limit the scope thereof.

In the following Examples, "%" means "w/v %" unless otherwise prescribed.

EXAMPLES

Example 1

A medium (pH 7.0, 60 ml) containing dextrin (1%), ammonium sulfate (0.2%), meast-S (1%), potassium dihydrogenphosphate (0.1%), magnesium sulfate (0.05%), calcium chloride (0.01%), ferrous sulfate (0.001%) and surfactant (trade name: KARARIN 102, manufactured by Sanyo Chemical Industries, Ltd., 0.1 v/v%), polyoxyethylene sorbitan monooleate (Tween 80) (0.5 v/v%) and an amino acid(1%) shown in Table 1 was placed in a 500-ml shaking flask and sterilized. Serratia marcescens Sr41 (FERM BP-487) was inoculated into the sterilized medium. The cultivation was carried out by shaking the medium(140 cpm) at 30° C. for 24 hours. The culture broth was centrifuged for 20 minutes to remove cells. Esterase was obtained as a crude enzyme solution.

Assay of Esterase Activity

The esterase activity was estimated according to the following method.

A mixture of 225 ml of 2% polyvinyl alcohol (Poval 117, manufactured by Kuraray Co., Ltd.) and 75 ml of olive oil was emulsified by stirring at 14,500 rpm at 5°–10° C. for 10 minutes. 5.0 ml of the olive oil-emulsion thus-obtained and 4.0 ml of 0.25M Tris-HCl buffer (pH 8.0, containing 2.5 mM calcium chloride) were preincubated at 37° C. for 10 minutes. One ml of an enzyme solution was added thereto to initiate enzymatic reaction. After the mixture was incubated at 37° C. for 20 minutes, 20 ml of a mixture of acetone-ethanol (1:1) were added to the reaction mixture to stop the enzymatic reaction. The mixture was titrated with 0.05N an aqueous sodium hydroxide solution by using phenolphthalein as the indicator. A control solution was prepared in the same manner as above except that acetone-ethanol (1:1) is added to the substrate solution before addition of the enzyme solution. Said control solution was titrated in the same manner as above. The amount of enzyme which was required to liberate 1 μmol of a fatty acid per minute was defined as one unit (U).

Results

The results are shown in the following Table 1.

TABLE 1

| Amino acid | Esterase activity (U/ml) |
| --- | --- |
| Sodium L-aspartate | 166.2 |
| Sodium L-glutamate | 160.2 |
| L-Proline | 170.3 |
| L-Histidine hydrochloride | 193.3 |
| L-Alanine | 115.9 |
| L-Threonine | 108.1 |
| L-Arginine | 67.6 |
| L-Serine | 87.8 |
| Glycine | 54.1 |
| (Control) None | 23.3 |

Example 2

A medium (pH 7.0, 60 ml) containing dextrin (1%), ammonium sulfate (0.2%), meast-S (1%), potassium dihydrogenphosphate (0.1%), magnesium sulfate (0.05%), calcium chloride (0.01%), ferrous sulfate (0.001%) and surfactant (trade name: KARARIN 102, manufactured by Sanyo Chemical Industries, Ltd., 0.1 v/v %), polyoxyethylene sorbitan monooleate (Tween 80) (0.5 v/v %) and an amino acid or amino acids shown in Table 2 was placed in a 500-ml shaking flask and sterilized. Serratia marcescens Sr41 (FERM BP-487) was inoculated into the sterilized medium. The cultivation was carried out by shaking the medium (140 cpm) at 30° C. for 24 hours. The culture broth was centrifuged for 20 minutes to remove cells. Esterase was obtained as a crude enzyme solution.

The esterase activity was estimated according to the assay method in Example 1.

Results

The results are shown in the following Table 2.

TABLE 2

| The amount of amino acid(s) | | Esterase activity (U/ml) |
| --- | --- | --- |
| L-Proline (%) | L-Histidine hydrochloride (%) | |
| 0 | 0.1 | 72.6 |
| 0 | 0.5 | 124.7 |
| 0 | 1.0 | 149.7 |
| 0.1 | 0 | 73.7 |
| 0.1 | 0.1 | 105.4 |
| 0.1 | 0.5 | 139.2 |
| 0.1 | 1.0 | 158.8 |
| 0.5 | 0 | 117.2 |
| 0.5 | 0.1 | 143.3 |
| 0.5 | 0.5 | 206.8 |
| 0.5 | 1.0 | 175.0 |
| 1.0 | 0 | 165.9 |
| 1.0 | 0.1 | 179.1 |
| 1.0 | 0.5 | 240.2 |
| 1.0 | 1.0 | 179.7 |
| (Control) | | |
| 0 | 0 | 20.6 |

Example 3

A medium (pH 7.0, 60 ml) containing dextrin (1%), ammonium sulfate (0.2%), meast-S (1%), potassium dihydrogenphosphate (0.1%), magnesium sulfate (0.05%), calcium chloride (0.01%), ferrous sulfate (0.001%) and surfactant (trade name: KARARIN 102, manufactured by Sanyo Chemical Industries, Ltd., 0.1 v/v %), L-proline (1%), L-histidine hydrochloride(1%) and a fatty acid(1%) shown in Table 3 was placed in a 500-ml shaking flask and sterilized. Serratia marcescens Sr41(FERM BP-487) was inoculated into the sterilized medium. The cultivation was carried out by shaking the medium (140 cpm) at 30° C. for 24 hours. The culture broth was centrifuged for 20 minutes to remove cells. Esterase was obtained as a crude enzyme solution.

The esterase activity was estimated according to the assay method in Example 1.

Results

The results are shown in the following Table 3.

TABLE 3

| Fatty acid | Esterase activity (U/ml) |
| --- | --- |
| Stearic acid | 159.5 |
| Oleic acid | 195.0 |
| Linoleic acid | 178.0 |
| Linolenic acid | 142.0 |
| (Control) None | 28.8 |

Example 4

A medium (pH 7.0, 60 ml) containing dextrin (1%), ammonium sulfate (0.2%), meast-S (1%), potassium dihydrogenphosphate (0.1%), magnesium sulfate (0.05%), calcium chloride (0.01%), ferrous sulfate (0.001%) and surfactant (trade name: KARARIN 102, manufactured by Sanyo Chemical Industries, Ltd., 0.1 v/v%), L-proline (1%), L-histidine hydrochloride (0.5%) and an ester (0.5%) shown in Table 4 was placed in a 500-ml shaking flask and sterilized. Serratia marcescens Sr41 (FERM BP-487) was inoculated into the sterilized medium. The cultivating was carried out by shaking the medium(140 cpm) at 30° C. for 24 hours. The culture broth was centrifuged for 20 minutes to remove cells. Esterase was obtained as a crude enzyme solution.

The esterase activity was estimated according to the assay method in Example 1.

Results

The results are shown in the following Table 4.

TABLE 4

| Fatty acid ester | Esterase activity (U/ml) |
|---|---|
| Sorbitan monolaurate | 148.8 |
| Sorbitan monomyristate | 155.2 |
| Sorbitan monostearate | 161.7 |
| Sorbitan tristearate | 152.2 |
| Sorbitan monooleate | 200.4 |
| Sorbitan trioleate | 208.7 |
| Polyoxyethylene sorbitan monolaurate | 185.0 |
| Polyoxyethylene sorbitan monomyristate | 187.2 |
| Polyoxyethylene sorbitan monostearate | 200.5 |
| Polyoxyethylene sorbitan monooleate | 199.0 |
| Polyoxyethylene sorbitan trioleate | 234.1 |
| (Control) None | 28.8 |

Example 5

A medium (pH 7.0, 60 ml) containing dextrin (2%), ammonium sulfate (0.2%), meast-S (0.2%), potassium dihydrogenphosphate (0.1%), magnesium sulfate (0.05%), calcium chloride (0.01%), ferrous sulfate (0.001%), polyoxyethylene sorbitan monooleate(Tween80) (0.1 v/v%) and surfactant (trade name: KARARIN 102, manufactured by Sanyo Chemical Industries, Ltd., 0.1 v/v%) and an amino acid shown in Table 5 (1%) was placed in a 500-ml shaking flask and sterilized. Serratia marcescens Sr41 (FERM BP-487) was inoculated into the sterilized medium. The cultivating was carried out by shaking the medium (140 cpm) at 30° C. for 24 hours. The culture broth was centrifuged for 20 minutes to remove cells. Esterase solution was obtained as a crude enzyme solution.

The esterase activity was estimated according to the assay method in Example 1.

Results

The results are shown in the following Table 5.

TABLE 5

| Amino acid | Esterase activity (U/ml) |
|---|---|
| Sodium L-aspartate | 25.2 |
| Sodium L-glutamate | 20.6 |
| L-Proline | 22.7 |
| L-Histidine hydrochloride | 26.1 |
| L-Alanine | 18.2 |
| L-Threonine | 18.1 |
| L-Arginine | 12.1 |
| L-Serine | 10.9 |
| Glycine | 11.4 |
| (Control) None | 5.3 |

EXAMPLE 6

A medium (60 ml) containing dextrin (1%), ammonium sulfate (0.2%), meast-S (1%), potassium dihydrogenphosphate (0.1%), magnesium sulfate (0.05%), calcium chloride (0.01%), ferrous sulfate (0.001%) and surfactant (trade name: KARARIN 102, manufactured by Sanyo Chemical Industries, Ltd., 0.1 v/v %), polyoxyethylene sorbitan monooleate (Tween 80) (0.5 v/v %) and L-proline (1%) was placed in a 500-ml shaking flask and sterilized. A strain of microorganism shown in Table 6 or 7 was inoculated into the sterilized medium. The cultivation was started at pH 7.0 (bacteria) or pH 6.0 (molds) and carried out by shaking the medium(140 cpm) at 30° C. for 24 hours. Esterase was obtained as in the same manner described in Example 1. (Assay of enzyme activity)

The esterase activity was estimated according to the following method.

The enzyme solution(10 μl) was added to a substrate solution(1 ml) of Lipase Kit S [Substrate: dimercaprol tributyrate, manufactured by Dainippon Pharmaceutical Co., Ltd.]. The mixture was incubated at 30° C. for 10 minutes, and then 5,5-dithiobis(2-nitrobenzoic acid) (color-producing agent) was added thereto. Enzyme activity was estimated by measuring the amount of the liberated 5-mercapto-2-nitrobenzoic acid at 412 nm.

The amount of enzyme which was required to liberate 1 μmol of 5-mercapto-2-nitrobenzoic acid per minute was defined as one unit(U).

Results

The results are shown in the following Tables 6 and 7.

TABLE 6

| Strain | Esterase activity (U/ml) L-proline | |
|---|---|---|
| | None | 1% |
| Absidia corymbifera IFO 4010 | 38 | 106 |
| Mucor angulimacrosporus IAM 6149 | 121 | 628 |
| Mucor javanicus IFO 5382 | 128 | 789 |
| Mucor lamprosporus IFO 6337 | 33 | 128 |
| Mucor subtilissimus IFO 6338 | 57 | 216 |

TABLE 7

| Strain | Esterase activity ($\times 10^3$ U/ml) L-proline | |
|---|---|---|
| | None | 1% |
| Corynebacterium alkanoliticum ATCC 21511 | 2.6 | 13.8 |
| Corynebacterium primorioxydans ATCC 31015 | 1.4 | 14.2 |
| Pseudomonas mutabilis ATCC 31014 | 3.0 | 9.9 |
| Pseudomonas putida ATCC 17453 | 2.2 | 7.6 |
| Serratia marcescens ATCC 27117 | 2.4 | 11.0 |
| Serratia primtica IAM 1255 | 0.2 | 32.6 |

Preparation

A medium (pH 7.0, 60 ml) containing dextrin (1%), ammonium sulfate (0.2%), meast-S (1%), potassium dihydrogenphosphate (0.1%), magnesium sulfate (0.05%), calcium chloride (0.01%), ferrous sulfate (0.001%) and surfactant (trade name: KARARIN 102, manufactured by Sanyo Chemical Industries, Ltd., 0.1 v/v %), polyoxyethylene sorbitan monooleate (Tween 80) (0.5 v/v %), L-proline (1.0%), and L-histidine hydrochloride (0.5%) was placed in a 500-ml shaking flask and sterilized. Serratia marcescens Sr41(FERM BP-487) was inoculated into the sterilized medium. The cultivation was carried out by shaking the medium(140 cpm) at 30° C. for 24 hours. The culture broth was centrifuged for 20 minutes to remove cells. Esterase was obtained as a crude enzyme solution.

To the esterase solution obtained above, toluene solution (1.5 l) of racemic methyl trans-3-(4-methoxyphenyl)glycidate (312 g) was added. The mixture was stirred at pH 8.0, 30° C. for 4 hours. After the reaction, organic phase was collected, washed with aqueous sodium bicarbonate to remove aldehyde, dried, and evaporated in vacuo to remove the solvent. The residue was recrystallized from isopropyl alcohol to yield methyl (2R, 3S)-3-(4-methoxyphenyl)glycidate (125 g) as colorless crystals.

$[\alpha]_D = -205.4°$

What is claimed is:

1. A process for producing an esterase by cultivating an esterase-producing microorganism, wherein the cultivation is carried out in a medium to which has been added an ester of sorbitan or polyoxyethylene sorbitan and a substituted or unsubstituted fatty acid having 12 to 18 carbon atoms, together with an amino acid which has the formula:

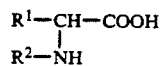
[I]

wherein $R^1$ is hydrogen or a lower alkyl group which may be substituted with a substituent selected from the group consisting of hydroxy, carboxy, amino, guanidino, carbamoyl, mercapto, methylthio, phenyl, hydroxyphenyl, imidazolyl and indolyl, and $R^2$ is hydrogen, or $R^1$ and $R^2$ are combined to form trimethylene.

2. The process according to claim 1, wherein the fatty acid ester is an ester of sorbitan or polyoxyethylene sorbitan and $C_{12-18}$ alkanoic acid, $C_{12-18}$ alkenoic acid, $C_{12-18}$ alkadienoic acid or $C_{12-18}$ alkatrienoic acid.

3. The process according to claim 1, wherein the fatty acid ester is selected from the group consisting of sorbitan monolaurate, sorbitan monomyristate, sorbitan monostearate, sorbitan tristearate, sorbitan monooleate, sorbitan trioleate, polyoxyethylenesorbitan monolaurate, polyoxyethylenesorbitan monomyristate, polyoxyethylenesorbitan monostearate, polyoxyethylenesorbitan tristearate, polyoxyethylenesorbitan monooleate, polyoxyethylenesorbitan trioleate.

4. The process according to claim 1, wherein the amount of the fatty acid or ester thereof is 0.1 g to 4 g per liter of medium.

5. The process according to claim 1, wherein the amino acid is selected from the group consisting of glycine, alanine, valine, leucine, isoleucine, serine, threonine, cysteine, arginine, asparagine, glutamine, aspartic acid, glutamic acid, phenylalanine, tyrosine, histidine, tryptophan, proline, lysine and methionine.

6. The process according to claim 1, wherein the amino acid is selected from the group consisting of glycine, alanine, threonine, proline, histidine, arginine, serine, glutamic acid and aspartic acid.

7. The process according to claim 1, wherein the amount of the amino acid is 0.1 g to 4 g per liter of the medium.

8. The process according to claim 1, in which the microorganism is a microorganism belonging to the genus Absidia, Mucor, Corynebacterium, Pseudomonas or Serratia.

* * * * *